US00PP31139P3

(12) United States Plant Patent
Lingle

(10) Patent No.: US PP31,139 P3
(45) Date of Patent: Nov. 26, 2019

(54) ULTRADWARF BERMUDAGRASS CALLED 'ACE DWARF'

(50) Latin Name: ***Cynodon dactylon*x*Cynodon transvaalensis* hybrid**
Varietal Denomination: ACE Dwarf Bermudagrass

(71) Applicant: GreensPerfection, LLC, Olive Branch, MS (US)

(72) Inventor: Rodney Lingle, Olive Branch, MS (US)

(73) Assignee: Greensperfection, LLC, Olive Branch, MS (US)

( * ) Notice: Subject to any disclaimer, the term of this patent is extended or adjusted under 35 U.S.C. 154(b) by 0 days.

(21) Appl. No.: 15/932,890

(22) Filed: May 16, 2018

(65) Prior Publication Data

US 2018/0338404 P1 Nov. 22, 2018

Related U.S. Application Data

(60) Provisional application No. 62/506,869, filed on May 16, 2017.

(51) Int. Cl.
*A01H 5/12* (2018.01)
*A01H 6/46* (2018.01)

(52) U.S. Cl.
USPC ..... Plt./389
CPC ..... *A01H 6/4612* (2018.05)

(58) Field of Classification Search
USPC ..... Plt./389
See application file for complete search history.

*Primary Examiner* — Annette H Para
(74) *Attorney, Agent, or Firm* — Baker Donelson

(57) ABSTRACT

The Bermudagrass Ultradwarf cultivar 'ACE Ultradwarf' (RL-1) is a new and distinct variety of bermudagrass hybrid cultivar that is highly suitable for golf greens and other closely mowed find turf surfaces.

15 Drawing Sheets

CROSS-REFERENCE TO RELATED APPLICATIONS

This application claims the benefit of and priority to U.S. Provisional Patent Application No. 62/506,869, filed on May 16, 2017, the content of such is hereby incorporated by reference in its entirety.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

Latin name of the genus and species of the plant claimed: *Cynodon dactylon*x*Cynodon transvaalensis* hybrid.

Varietal denomination: 'ACE Dwarf' Bermudagrass.

The cultivar is especially suited for golf courses, golf greens, athletic fields, race courses, recreational parks, and/or residences.

BACKGROUND OF THE INVENTION

Bermudagrass (*Cynodon* spp. L. C. Rich) is one of the most important and widely used warm-season turfgrasses. It is adapted to the warm- and subtropic-climatic regions of the world. The turf-type Bermudagrasses are $C_4$, perennials that originated in southeastern Africa.

SUMMARY OF THE INVENTION

The invention is directed to a new Bermudagrass variety, called 'ACE Dwarf' Bermudagrass.

An aspect of the invention is directed to a new and distinct Bermudagrass plant, substantially as herein shown, illustrated, and described.

An aspect of the invention is directed to a Bermudagrass Ultradwarf hybrid cultivar substantially as herein shown, illustrated, and described, wherein the cultivar is selected for resistance to an herbicide. In one embodiment, the herbicide is a glyphosate-containing herbicide. In another embodiment, the herbicide is Roundup™.

An aspect of the invention is directed to a Bermudagrass Ultradwarf hybrid cultivar, substantially as herein shown, illustrated, and described, wherein the cultivar is selected for cold tolerance to temperatures of about 20° F. to about 38° F. In some embodiments, the temperature is about 25° F. to about 32° F. In some embodiments, the temperature is about 20° F., about 21° F., about 22° F., about 23° F., about 24° F., about 25° F., about 26° F., about 27° F., about 28° F., about 29° F., about 30° F., about 31° F., about 32° F., about 33° F., about 34° F., about 35° F., about 36° F., about 37° F., about 38° F., about 39° F., or about 40° F. In some embodiments, the temperature is below 20° F. In some embodiments, the temperature is above 40° F. (for example, about 41° F., about 42° F., about 43° F., about 44° F., about 45° F., about 46° F., about 47° F., about 48° F., about 49° F., or about 50° F.).

An aspect of the invention is directed to a Bermudagrass Ultradwarf hybrid cultivar, wherein the cultivar is selected for frost tolerance to temperatures of about 28° F. to about 48° F. In some embodiments, the temperature is about 32° F. to about 40° F. In some embodiments, the temperature is about 28° F., about 29° F., about 30° F., about 31° F., about 32° F., about 33° F., about 34° F., about 35° F., about 36° F., about 37° F., about 38° F., about 39° F., about 40° F., about 41° F., about 42° F., about 43° F., about 44° F., about 45° F., about 46° F., about 47° F., about 48° F., or about 49° F. In some embodiments, the temperature is below 32° F. In some embodiments, the temperature is above 40° F. (for example, about 41° F., about 42° F., about 43° F., about 44° F., about 45° F., about 46° F., about 47° F., or about 48° F.).

An aspect of the invention is directed to a Bermudagrass Ultradwarf hybrid cultivar, wherein the cultivar is selected for resistance to a glyphosate-containing herbicide and for cold tolerance to temperatures of about 20° F. to about 38° F. In one embodiment, the herbicide is a glyphosate-containing herbicide. In another embodiment, the herbicide is Roundup™. In some embodiments, the temperature is about 25° F. to about 32° F. In some embodiments, the temperature is about 20° F., about 21° F., about 22° F., about 23° F., about 24° F., about 25° F., about 26° F., about 27° F., about 28° F., about 29° F., about 30° F., about 31° F., about 32° F., about 33° F., about 34° F., about 35° F., about 36° F., about 37° F., about 38° F., about 39° F., or about 40° F. In some embodiments, the temperature is below 20° F. In some embodiments, the temperature is above 40° F. (for example, about 41° F., about 42° F., about 43° F., about 44° F., about 45° F., about 46° F., about 47° F., about 48° F., about 49° F., or about 50° F.).

BRIEF DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
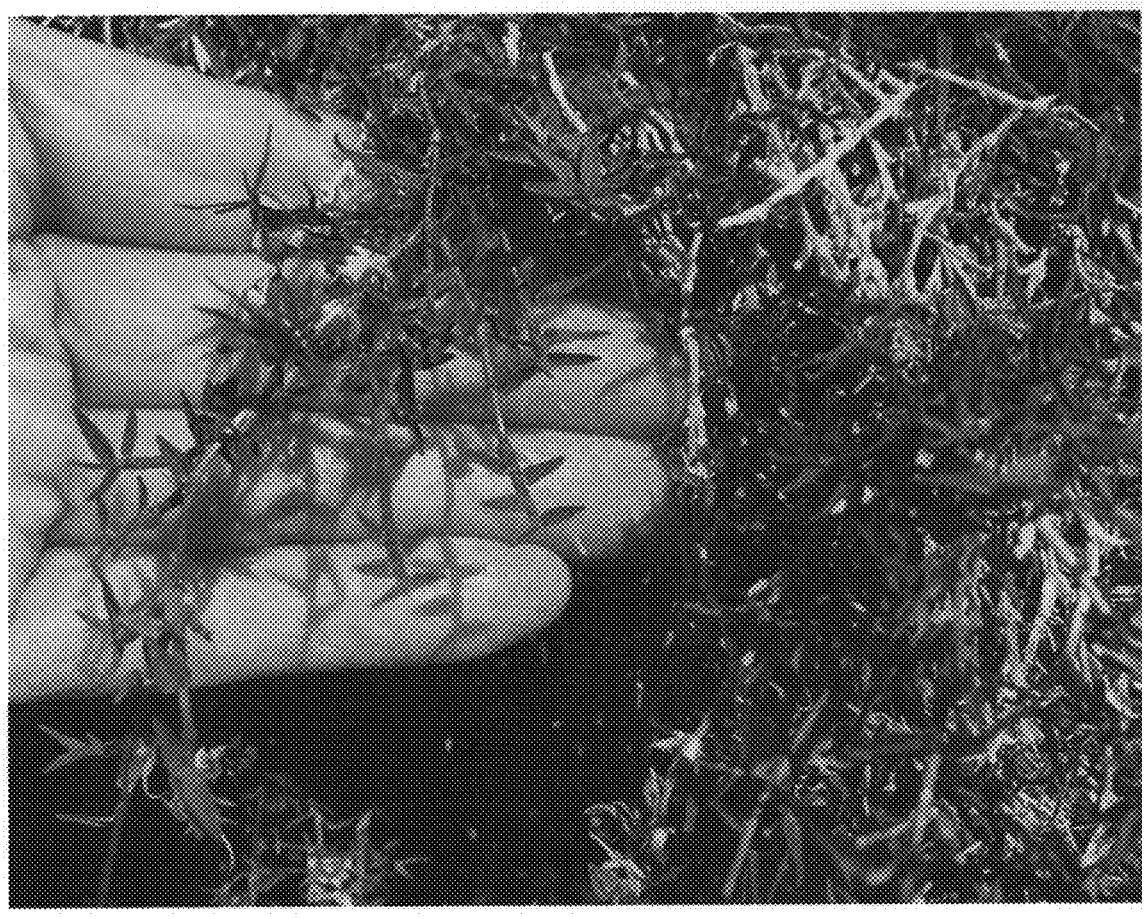
FIG. 1 is a photograph of a hybrid bermudagrass cultivar, named ACE Dwarf (also referred to herein as RL-1, and MACH-1) grown in a pot after identified and excised from a golf green. This image shows growth for 2 years without mowing and/or trimming.

The present invention is directed to a new and distinct Bermudagrass hybrid plant. A hybrid bermudagrass cultivar, named 'ACE DWARF' (also referred to herein as RL-1), is different from and morphologically advantageous compared to other Bermudagrass cultivars. 'ACE DWARF' is distinguished by a very high rate and density of lateral stem development, a very low vertical growth characteristic due to the extremely short internode length, a very short leaf length, a very low terminal height growth, fine leaf width, and no seedhead development.

The common turf-type species of *Cynodon* include, but are not limited to *Cynodon dactylon* (L.) Pers. or *dactylon* Bermudagrass, which is a tetraploid (4n); and *Cynodon transvaalensis* (Burtt-Davy) or African Bermudagrass, which is a diploid (2n).

The *dactylon* Bermudagrasses are characterized by a relatively coarse leaf width and lower shoot density. Without being bound by theory, the hybrid bermudagrasses have a more narrow leaf width and a higher shoot density, lower terminal height, and shorter internode length.

Historically, two Bermudagrass varieties have been utilized on golf greens, Tifgreen and Tifdwarf. In the late 1990s, however, use of Champion Bermudagrass and other Ultradwarf Bermudagrasses became the most widely used on golf greens. Non-limiting examples of Ultradwarf Bermudagrasses include Floradwarf (PP 9,030), Champion (PP 9,888), Tifeagle (PP 11,163), Mississippi Supreme (PP 11,781), and Minverde (PP 12,084). Although Ultradwarf Bermudagrasses can allow for lower greens mowing heights, their growth characteristics present challenges for greens and turf maintenance and management. The aspects of these grasses' growth habits, which can be problematic, include without limitation very high shoot density, lateral growth which is comprised almost entirely of stolons, and shallow rooting. Due to very limited rhizome production, these grasses have less energy storage sites and therefore recovery from injury can be more slower than larger Bermudagrasses.

There are six components for assessing turfgrass quality: (a) uniformity, (b) density, (c) texture, (d) growth habit, (e) smoothness, and (f) color. These aspects will be discussed in further detail below. Color notations as discussed herein can be affected by light quality and fertility as well as general plant growth. All color designations denoted herein were obtained using the RHS Colour Chart (Fifth edition, 2007) Certain characteristics of the new plant may vary depending on the age of the plant, such that characteristics such as dimensions, sizes, and/or colors are approximations or averages since the variety has not been observed under every possible environmental condition. Therefore, as will be apparent to those skilled in the art, the phenotype of the new cultivar can differ from the descriptions depending upon environmental variations, which include but are not limited to, the season, climate, soil, temperatures, day lengths, light direction and quality, and fertilization, as well as other factors. The photographs and the detailed description of the invention are intended to illustrate further the invention and its advantages.

Abbreviations and Definitions

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Origin of the Cultivar

The genotype 'ACE DWARF' variety is a new and distinct natural turfgrass cultivar that was selected from a segregated patch of grass found on a cultivated golf green in Memphis, Tenn. in 1998. As with many other popular varieties of golf greens, 'ACE DWARF' appears to have developed from a natural mutation of the parental Bermuda green. This new and distinct cultivar was noticed because of the dwarfness of the variety. The golf green had been originally planted with Tifdwarf hybrid Bermudagrass (*Cynodon dactylon*x*Cynodon transvaalensis*) in the early 1970s. As compared to the parental Tifdwarf green from which 'ACE DWARF' was selected. 'ACE DWARF' is a much finer grass with shorter internodes and a dwarf growth habit.

Figure 15:
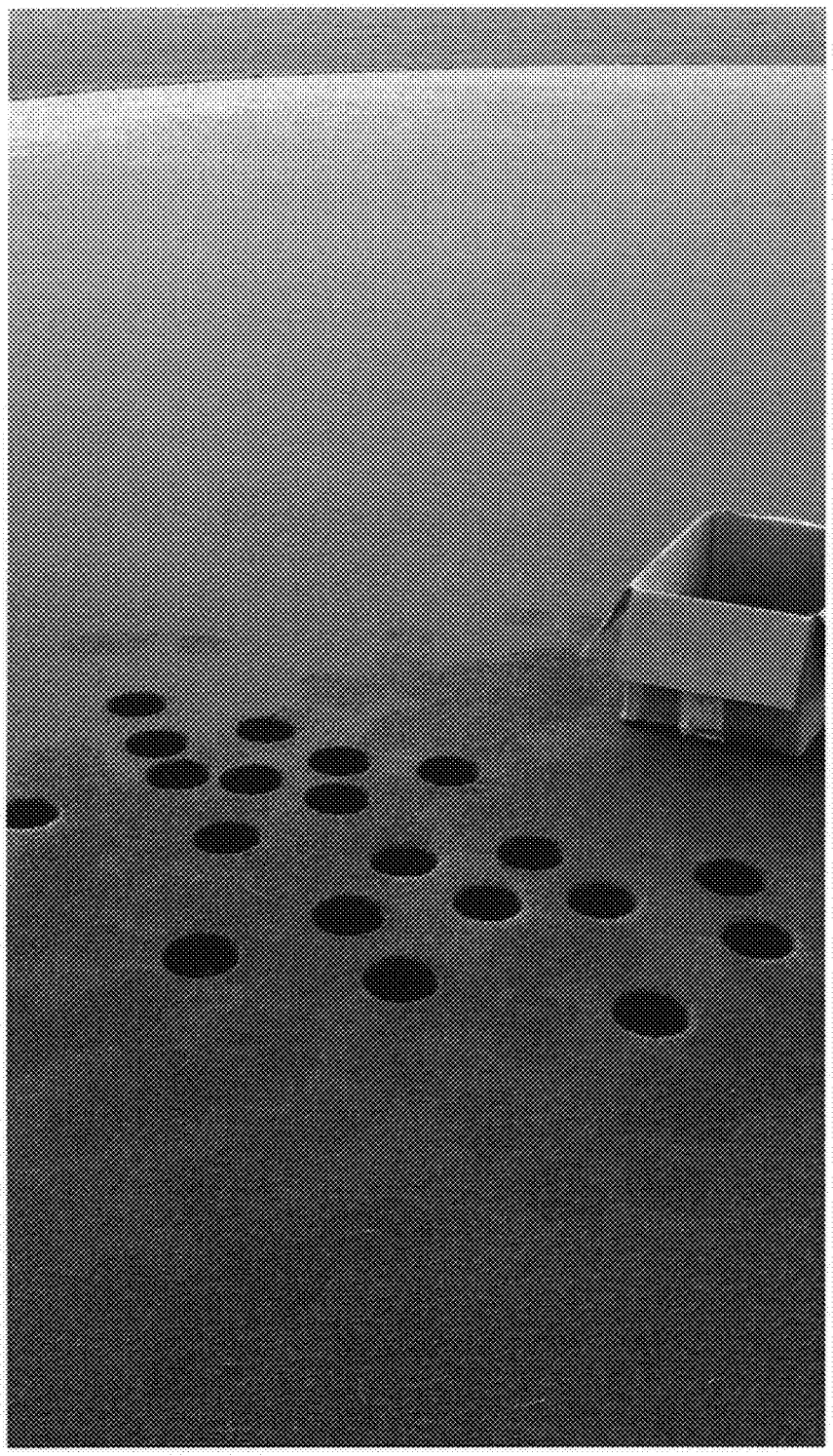
FIG. 15 is a photograph showing a six-year old test green at the inventor's home in Olive Branch, Miss.

For the first asexual propagation, the 'ACE DWARF' grass was extracted from the cultivated golf green in Memphis, Tenn. as a single sprig comprising a short lateral stem with multiple nodes and placed in a moist paper towel. The single sprig was then planted in a one-gallon pot with sterilized soil and transferred to inventor's facility/property in Olive Branch, Miss. to begin expansion. All expansion was performed from the growth of this original sprig, in Olive Branc, Miss. It was then further cut into individual sprigs and planted in 2 gallon pots. This was then propagated into a 1500 sq. ft. growth area. This 150 sq. ft. lawn of 'ACE DWARF' was managed under golf course conditions and very close mowing to confirm the purity of the grass. Grasses developed for golf greens must be managed at close mowing heights to reveal any mutations in the grass. If grasses are selected at terminal height, it is very difficult to determine their purity. After six years of intense grass management, no mutations were observed (see FIG. 15).

Taxonomy

'ACE DWARF' is a triploid hybrid Bermudagrass (*Cynodon dactylon*x*Cynodon transvaalensis*). It is taxonomically identified as *Cynodon*x*magennis* ii.

Morphological Characterization

Morphological characteristics measured include internode length, stolon diameter, leaf length and width, and the leaf length:width ratio. Measurements were made between the third and fourth node and on the outer leaf from the third node using digital calipers.

Compared to other ultradwarf Bermudagrasses, 'ACE DWARF' has a higher shoot density, thatch production that is similar to other ultradwarfs, rhizome development that is similar to other ultradwarfs, normal rooting, and has prolific stolon production with slightly larger stolon diameter. Rooting depth for 'ACE DWARF' is normal. 'ACE DWARF' has more lateral stems in comparison to other ultradwarf Bermudagrasses. The leaf blade color of 'ACE DWARF' is medium (N135A) to dark green (N134A) depending upon fertilization. Color is described with more specificity below.

This new and distinct combination of morphological characteristics has been successfully retained through multiple generations of asexual vegetative propagation. These traits make 'ACE DWARF' useful for golf greens, lawn bowling courts, and tennis courts. The quantitative assessments provided below were obtained from 'ACE DWARF' (RL-1) that was cultivated within a 6-inch pot in a greenhouse located in Camden, S.C. The 'ACE DWARF' (RL-1) was approximately 1 year of age at the time of quantification.

Leaf Blade Width. Quantitative assessments of leaf blade widths showed 'ACE DWARF' (RL-1) to have a smaller leaf blade width and very fine canopy texture. The leaf blade width of 'ACE DWARF' (RL-1) was more fine than three hybrid ultradwarf Bermudagrass cultivars, being 8.7% less wide than Champion and MiniVerde (see Table 1), and being 12.5% less wide than TifEagle (see Table 1).

TABLE 1

Measurements of leaf blade widths.

| Grass | Leaf Blade Width (atm) |
|---|---|
| Champion | 2.3 |
| Mini Verde | 2.3 |

TABLE 1-continued

| Measurements of leaf blade widths. | |
|---|---|
| Grass | Leaf Blade Width (atm) |
| TifEagle | 2.4 |
| RL-1 | 2.1 |

Leaf Blade Length. Quantitative assessments of leaf blade lengths showed 'ACE DWARF' (RL-1) to have a very short leaf blade length. The leaf blade length of 'ACE DWARF' (RL-1) was dramatically shorter than three hybrid ultradwarf Bermudagrass cultivars, being 67.6% shorter than Champion (conversely, Champion being 308.5% longer than ACE), 74.3% shorter than MiniVerde (conversely, MiniVerde being 389.4% longer than ACE), and 73.1% shorter than TifEagle (conversely, TifEagle being 372.3% longer than ACE) (see Table 2).

TABLE 2

| Measurements of leaf blade lengths. | |
|---|---|
| Grass | Leaf Blade Length (mm) |
| Champion | 14.5 |
| Mini Verde | 18.3 |
| TifEagle | 17.5 |
| RL-1 | 4.7 |

Leaf Blade Length to Blade Width Ratio. Quantitative assessments of leaf blade length to length blade width ratios showed 'ACE DWARF' (RL-1) to have a decreased leaf blade:width ratio. The leaf blade length to length blade width ratio of 'ACE DWARF' (RL-1) was substantially less than three hybrid ultradwarf Bermudagrass cultivars, being 65.6% less than Champion, 72.5% less than MiniVerde, and 69.9% less than TifEagle (see Table 3).

TABLE 3

| Measurements of Leaf Blade Length to Blade Width Ratios. | |
|---|---|
| Grass | Leaf Blade Length::width |
| Champion | 6.4 |
| MiniVerde | 8.0 |
| TifEagle | 7.3 |
| RL-1 | 2.2 |

Internode Length. Quantitative assessments of internode lengths showed 'ACE DWARF' (RL-1) to have a much shorter internode length. The internode length of 'ACE DWARF' (RL-1) was significantly shorter than three hybrid ultradwarf Bermudagrass cultivars, being 54.1% shorter than Champion, 56.8% shorter than MiniVerde, and 57.3% shorter than TifEagle (see Table 4).

TABLE 4

| Measurements of Internode Length. | |
|---|---|
| Grass | Internode Length (mm) |
| Champion | 46.4 |
| MiniVerde | 49.3 |
| TifEagle | 49.9 |
| RL-1 | 21.3 |

Stolon Diameter. Quantitative assessments of stolon diameters showed 'ACE DWARF' (RL-1) to have a slightly wider stolon diameter. The Stolon Diameter of 'ACE DWARF' (RL-1) was wider than three hybrid ultradwarf Bermudagrass cultivars, being 11.5% greater than Champion, 8.0% greater than MiniVerde, and 12.6% greater than TifEagle (see Table 5). Without being bound by theory, having a slightly wider stolen can be advantageous for energy storage and in injury recuperative ability. 'ACE DWARF' (RL-1) has far less rhizomes than the older 328 Bermudagrass and therefore the 'ACE DWARF' (RL-1) stolons become important in providing storage sites. Without being bound by theory, the wider stolons can also be helpful when harvesting sprigs to vegetatively plant 'ACE DWARF' (RL-1).

TABLE 5

| Measurements of Stolon Diameter. | |
|---|---|
| Grass | Stolon Diameter (mm) |
| Champion | 0.77 |
| MiniVerde | 0.80 |
| TifEagle | 0.76 |
| RL-1 | 0.87 |

Inflorescence. No inflorescence were observed for 'ACE DWARF' (RL-1) as compared to three hybrid ultradwarf Bermudagrass cultivars.

Color. All color designations denoted herein were obtained using the RHS Colour Chart (Fifth edition, 2007). The color of 'ACE DWARF' (RL-1) can vary from brilliant yellowish green (140B) to dark green (N134A), depending upon the grass management and how the micronutrients are applied. The fertility level and growing conditions of the soil in which 'ACE DWARF' (RL-1) is cultivated strongly influences the plant's color. 'ACE DWARF' responds extremely well to fertilization and is a very efficient user of nitrogen. As such, degree of fertilization, including the natural fertility levels of the soil, rather than the age of the plant, is the primary determinant for the plant's color. Color can be managed to the individual's liking. For instance, if the 'ACE DWARF' (RL-1) is not fertilized or under fertilized blades of the plant are green (134A) in color. By contrast, when heavily fertilized or fertilized with magnesium, iron, or manganese, the blades of 'ACE DWARF' (RL-1) can be dark green (N134A) in color. The stolons and internodes can be brilliant yellowish green (140B) in color. In embodiments, the stolons and leaves do not express anthocyanin pigmentation in the fall.

'ACE DWARF' (RL-1) Turf Green Characterization and Management. Compared to other ultradwarf Bermudagrasses, 'ACE DWARF' (RL-1) distinguishes itself with a very high shoot density, shorter internode length, small leaf length to width ratio and an exceptionally low terminal height. These characteristics are what give 'ACE DWARF' (RL-1) its velvety texture and extremely smooth ball roll when managed correctly. Management observations have also demonstrated the ability of 'ACE DWARF' (RL-1) to be mowed at very low mowing heights, which is an absolute necessity for achieving today's requirement for very fast putting greens speed.

Because 'ACE DWARF' (RL-1)'s canopy is dense, there is a need to properly manage the grass for thatch production and canopy density. Without being bound by theory, an effective way to manage such canopy density and thatch production is through light and frequent topdressing in combination with light and frequent vertical mowing during the growing season. Proper Nitrogen fertilization is also a key component in this management system. The best Nitrogen management requires that only the necessary amount of Nitrogen should be applied to keep the turf canopy dense, but not overly puffy or thick. All ultradwarf turf will develop excessive thatch when overly fertilized with excess Nitrogen.

Without being bound by theory, when modern golf greens become too thick and thatchy, the greens tend to restrict the infiltration of water. However, this problem can be overcome by proper surface management and the use of a soil wetting agent (e.g., a soil surfactant). The use of soil wetting agents have become an industry standard in golf greens management with the new ultradwarf grasses in order to increase infiltration of water coupled with specific morphological characteristics that are expressed by ultradwarf bermudagrass cultivars.

Without being bound by theory, turf/greens grasses can develop grain if not properly managed. This is a response to phenotypic plasticity and can be proven. The way to prevent all grain development is through the use of changing mowing directions daily in conjunction with rotary brushes and light frequent vertical mowing. If a grass plant is mowed in a single direction every day, it will develop grain going in the direction of travel.

Representative Detailed Characteristics. A detailed description of the new and distinct genotype of hybrid Bermudagrass named 'ACE DWARF' (RL-1) includes:

1. the leaf length is about 4-5 mm;
2. the internode length of stolons is about 21-22 mm;
3. the leaf width is about 2.1 mm under very close mowing;
4. no inflorescence is produced; and
5. no seeds are produced.

Performance Characterization

Herbicide Resistance.

Resistance to grass herbicides can provide a highly effective means of controlling weedy grasses in various turf grass species. Exclusion of undesirable weedy grasses can be accomplished by treating the area in which exclusive growth of resistant plant species is desired, with herbicides to which resistance has been established.

As used herein, "herbicide-resistant" or "herbicide-tolerant," including any of their variations, can refer to the ability of a plant to recover from, survive and/or thrive after contact with an herbicide in an amount that is sufficient to cause retardation of growth or death of a non-resistant plant of the same species.

In some embodiments, the herbicide can be contacted directly to the herbicide-resistant plant and to the weeds. For example, the herbicide can be dusted, foamed, waxed, rubbed, and/or sprayed, directly over the herbicide-resistant plant and the weeds. In one embodiment, the herbicide can be applied in granular form directly over the herbicide-resistant plant and the weed. Alternatively, the herbicide can be sprayed directly on the herbicide-resistant plant and the weeds. Other means by which the herbicide can be applied to the herbicide-resistant plant and weeds include, but are not limited to, dusting or spraying over an area or plot of land containing the herbicide-resistant plant and the weeds.

In some embodiments, the herbicide can be contacted or added to a growth medium in which the herbicide-resistant plant and the weeds are located. The growth medium can be, but is not limited to, soil, peat, dirt, mud, or sand. In other embodiments, the herbicide can be included in water with which the plants are irrigated.

As described herein, 'ACE DWARF' (RL-1) has herbicide-resistant characteristics as compared to other Bermudagrass cultivars. In some embodiments, 'ACE DWARF' (RL-1) can withstand the immediate effect of growth inhibition caused by selective herbicides (e.g., herbicides that include the active ingredient fluazifop (i.e., Fusilade, Ornamec, and Grass-B-Gon), or clethodim (i.e., Envoy)) and/or non-selective herbicides (e.g., Glyphosate (i.e., Roundup)). Representative examples of herbicides that can control the growth of Bermudagrass cultivars include, but are not limited to, ureas, sulfonylureas, glyphosate, (2,4-dichlorophenoxy)acetic acid (2,4D), acetochlor, alachlor, anilofos, butachlor, benfuresate, cafenstrole, dimethenamid-P, fentrazamide, indanofan, Imazaquin, Imazamox, Imazapic, Imazapyr, flufenacet, mefenacet, s-metolachlor, molinate, pethoxamid, pretilachlor, prosulfocarb, pyroxasulfone, thenylchlor, Triclopyr Amin, and thiobencarb. In one embodiment, a combination of herbicides disclosed herein can be used to control growth of Bermudagrass cultivars. In one embodiment, a combination of herbicides disclosed herein can be used to control growth of 'ACE DWARF' (RL-1). Growth regulators as understood by the skilled artisan can also be used to control growth of Bermudagrass cultivars (e.g., 'ACE DWARF' (RL-1)) which include, but are not limited to Trinexapac-ethyl, Flurprimidol, Mefluidide, Paclobutrazol, Ethephon, and Prohexadione Calcium.

Pesticides.

Representative examples of pesticides that can readily control the growth of bermudagrass cultivars, but not necessarily 'ACE DWARF' (RL-1) include, but are not limited to, fluazifop (i.e., Fusilade,) and Glyphosate (i.e., Roundup) .

Cold Tolerance and Frost Tolerance.

Environmental stress such as low temperature threaten the survival of plants, especially those unable to withstand these types of extreme conditions. For example, warm season grasses (e.g. Bermudagrass, St. Augustine grass, etc.) will grow as rich green carpets in colder northern regions of the U.S. during the warm summer months but then during the fall and winter they wither, turn brown and become dormant and frequently die from cold temperatures, thus requiring seasonal reseeding or resodding, and the like in the spring.

As used herein, "cold tolerance," "freeze tolerance," "cold hardiness," and "response to cold" can refer to the ability of a plant to live at or following exposure to a low temperature (e.g., its survivability).

As used herein, "frost tolerance" can refer to the length of time a plant is able to maintain its green color as the fall and winter months set in and conversely, the length of time a plant is able to regain its green color as the spring months approach (e.g., how quick the plant is able to recover from dormancy).

As described herein, 'ACE DWARF' (RL-1) has cold tolerance characteristics as compared to other Bermudagrass cultivars (see Example 3 herein).

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

As will be apparent to one of ordinary skill in the art from a reading of this disclosure, the embodiments of the present disclosure can be embodied in forms other than those specifically disclosed above. The particular embodiments described herein are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—DNA Analysis of RL-1 ('ACE DWARF')

Bermudagrass cultivars, such as Champion, Mini Verde, TifEagle, TifWay, and TifDwarf, were used as controls for testing the unknown sample of RL1 ('ACE DWARF'). Leave tissues of control cultivars were all collected from plants grown in the USDA greenhouse in Tifton, Ga.

Figure 2:
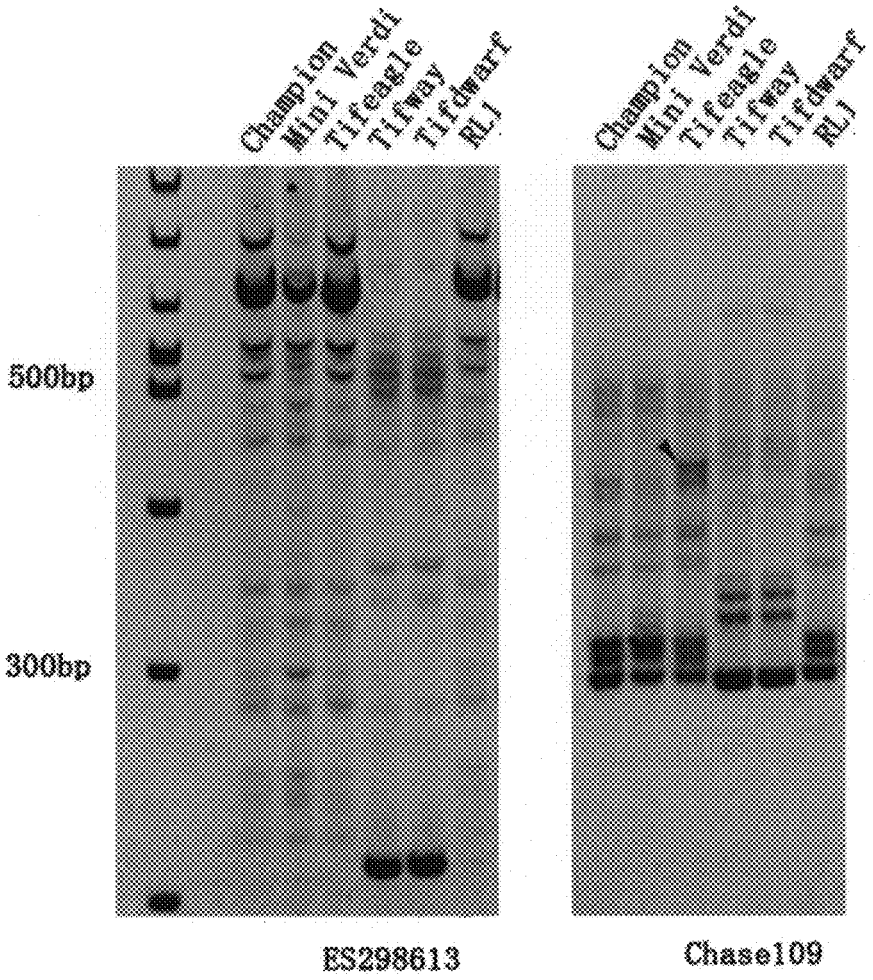
FIG. 2 is a photograph of a DNA gel.

Methods. Genetic DNA was extracted using CTAB method and quantified using Nanodrop 2000i. All DNA was diluted to 50 ng/ul. PCR was carried out with 23 polymorphic SSR makers. Chase 109 and ES298613 were the most informative SSR markers for the investigated cultivars and gel images from these markers are shown in FIG. 2.

Results. DNA test results showed that RL1 is Champion type and using these markers RL1 is indistinguishable from Champion. Champion and Mini Verdi are very close genetically, however there are minor differences between them (see box on gel profile of ES298613).

When using DNA fingerprinting, it is possible to state that two lines are genetically different but it is never possible to say with absolute certainty that two lines are genetically identical, since all possible markers and comparisons have not been made. Without being bound by theory, RL-1 is indistinguishable from Champion using ES298613 and Chase 109 markers. Without being bound by theory, RL-1 can be genetically different from Champion once a marker that will distinguish them has been identified. RL-1 ('ACE DWARF') morphologic and physical phenotypes as discussed herein indicate genetic differences as compared to Champion.

Example 2—Roundup tolerance of RL-1 ('ACE DWARF')

A Roundup application was applied 3 times to a small plot of RL-1 that was no longer being used. The application rates and timing were as follows:

1st application (May 15, 2015): Concentration of Glyphosate in Roundup Application was 4% of the solution;

2nd application (Jun. 1, 2015): Glyphosate at 4% concentration; and

3rd application (Jun. 20, 2015): Glyphosate at 4% concentration

After the first application of Glyphosate, 'ACE DWARF' (RL-1) did not show the severity of injury that had been initially observed with the first applications that were associated with other Bermudagrass Ultradwarf cultivars.

Surprisingly, after two applications of Glyphosate, a significant amount of live material remained in the plot, about 25% of 'ACE DWARF' (RL-1) as compared to other Bermudagrass cultivars, such as Champion and MiniVerde. After 3 applications, 'ACE DWARF' (RL-1) still displayed green leafs in the canopy at about 5%.

The concentration of Glyphosate to kill Bermudagrasses according to manufacturer's instructions comprises 2% of the solution applied. Bermudagrass Ultradwarf cultivars, such as MiniVerde, Champion, and TifEagle, on golf greens were killed using the technique described above. Ultradwarf Bermudagrass cultivars, such as MiniVerde, Champion, TifEagle, did not survive after 3 applications of Glyphosate at 4% concentration.

A comparative Glyphosate application will also be conducted to observe how 'ACE DWARF' (RL-1) compares to two other Bermudagrass Ultradwarf cultivars MiniVerde and TifEagle. A 1% concentration and a 2% concentration of Glyphosate will be used in these studies since those are the concentrations as directed by the manufacturer's label. Glyphosate is not effective on dormant turf, only actively growing green tissue thus the study will not be conducted during the winter months.

Example 3—Cold tolerance of RL-1 ('ACE DWARF')

Figure 3:
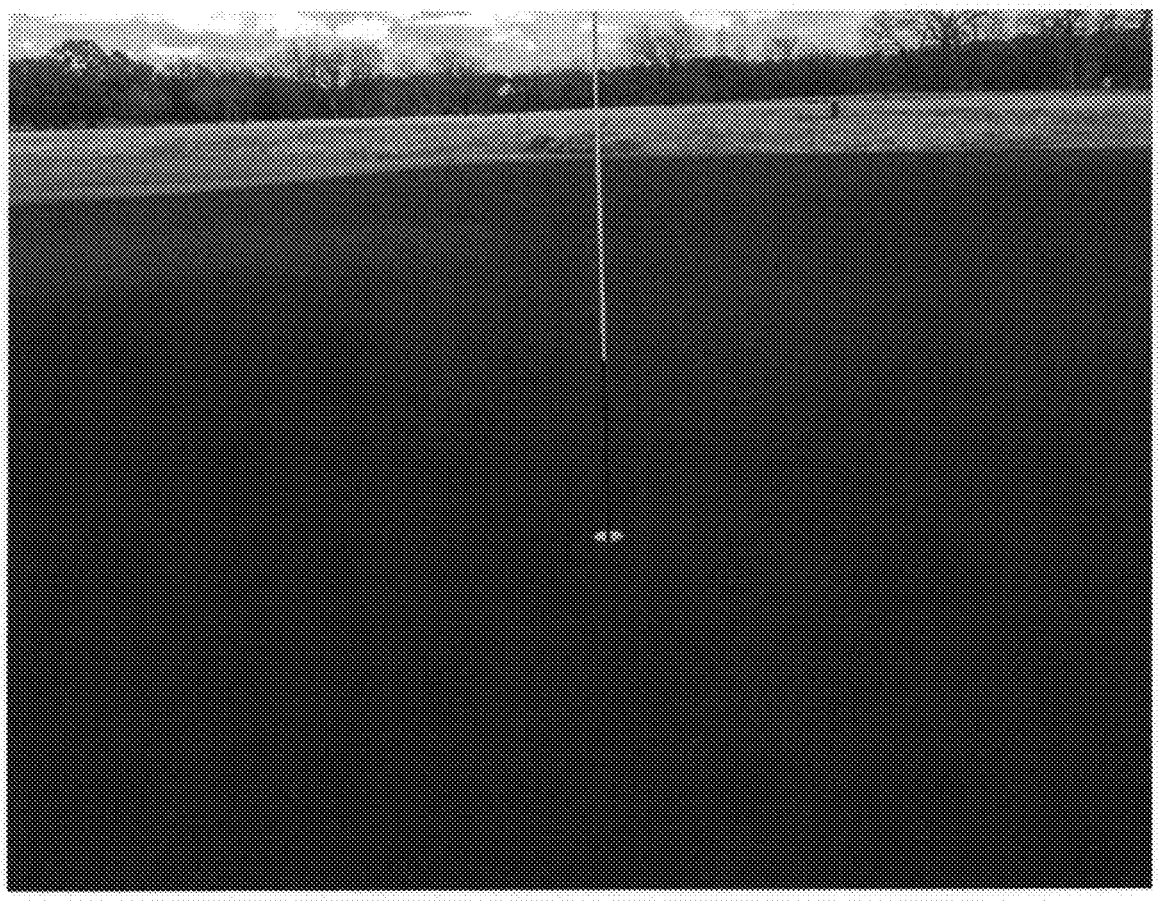
FIG. 3 is a picture of "purple spots" appearing on Bermudagrass cultivar Champion. These spots do not appear on ACE Dwarf in response to cold exposures.
Figure 4:
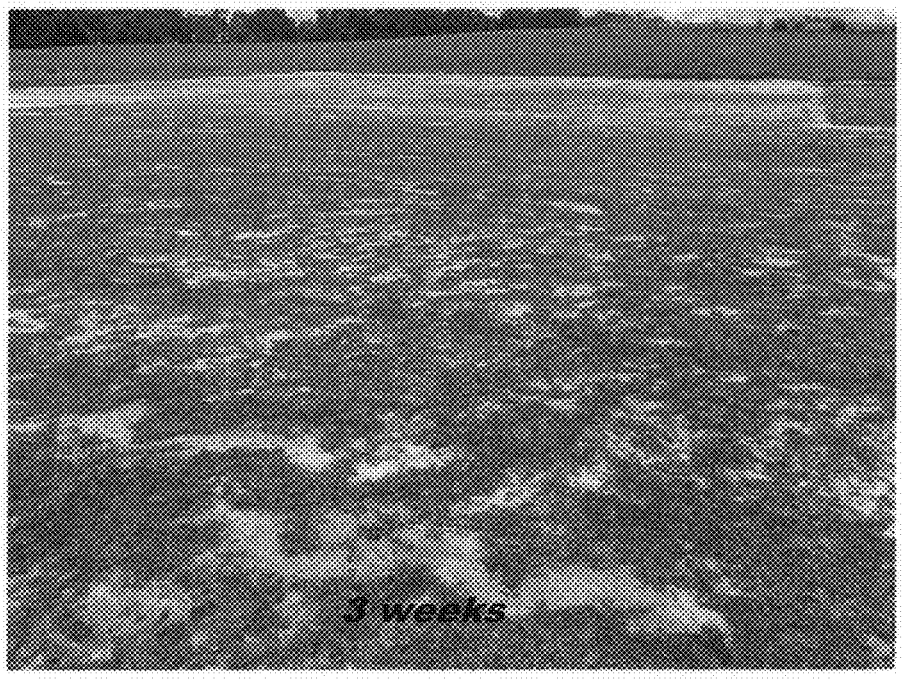
FIG. 4 are photographs of RL-1 planted on May 22, 2017. The RL-1 cultivar is in the foreground with Tifeagle in the background. The TOP image was taken at 3 weeks and the Bottom image was taken at 5 weeks. Both bermudagrass cultivars were planted on the same day.
Figure 4:
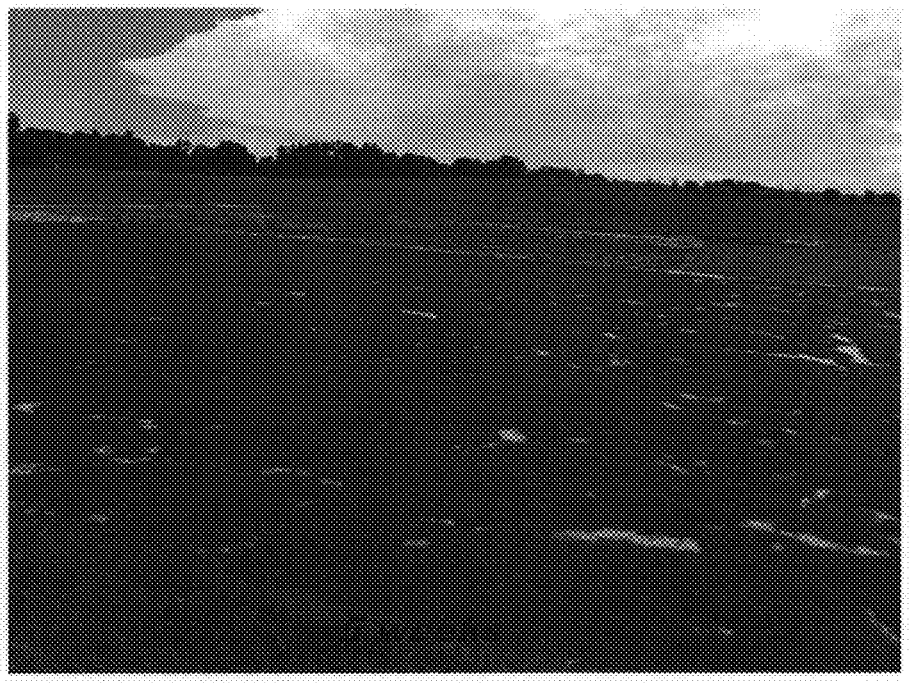
Figure 5:
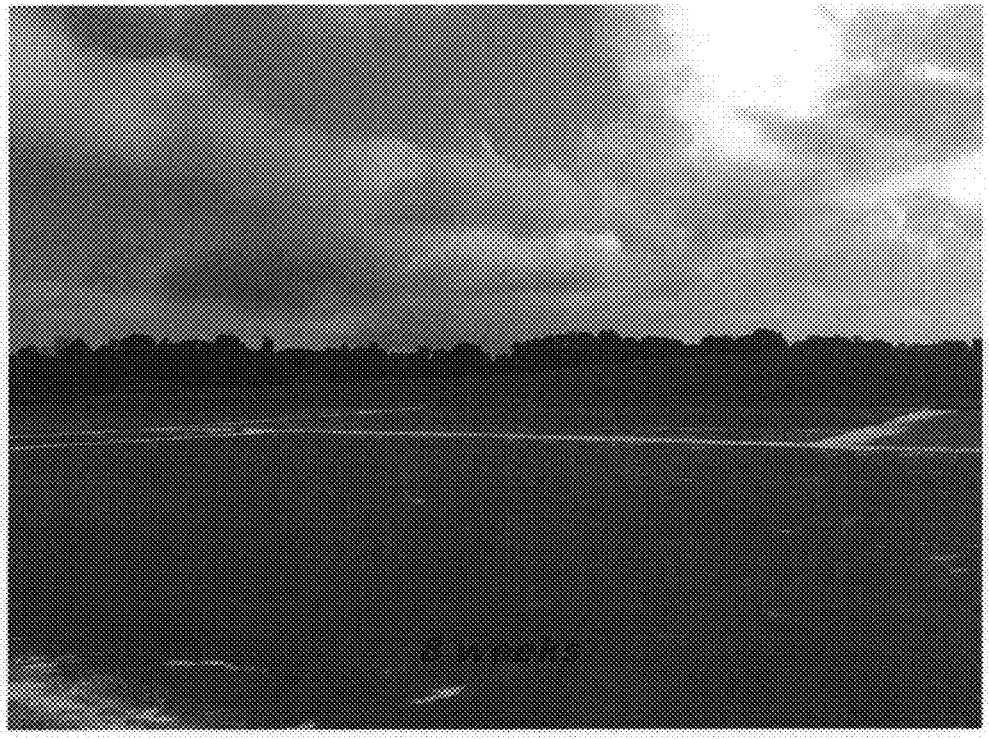
FIG. 5 are photographs of RL-1 taken at 8 weeks (top) and twelve weeks (bottom).
Figure 5:
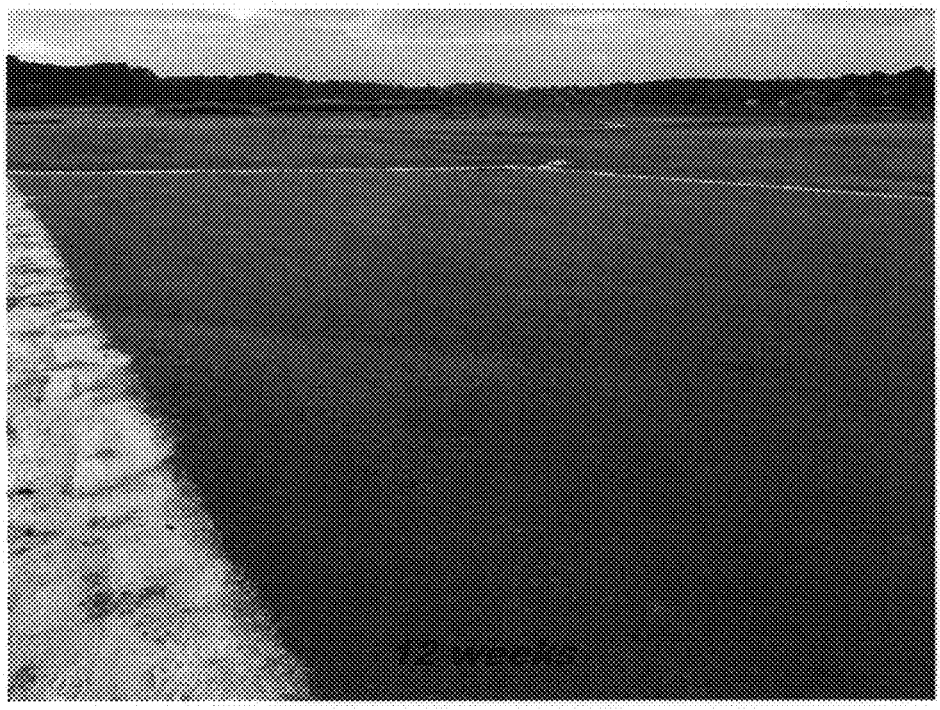
Figure 6:
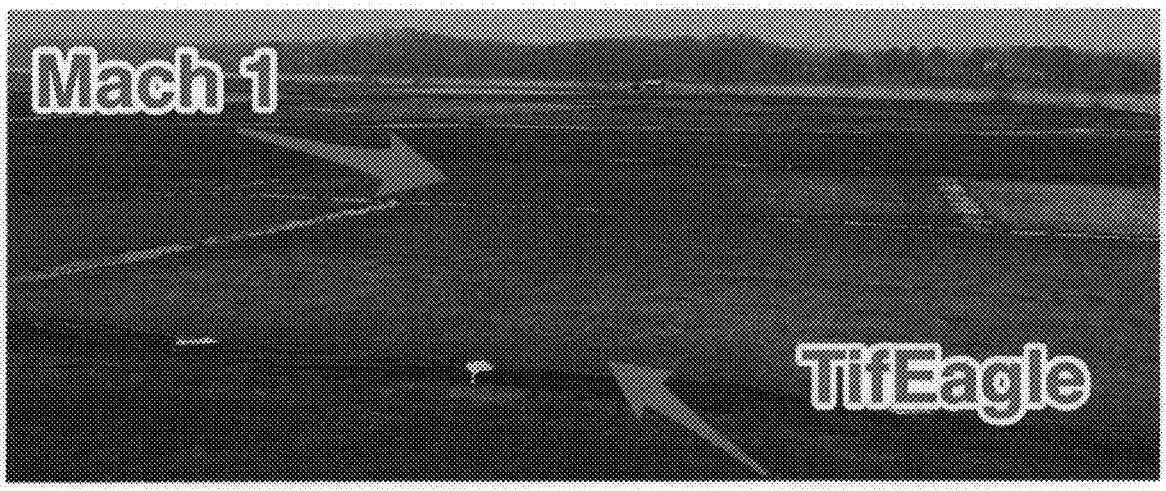
FIG. 6 (TOP Photograph) The image with the arrows indicates the bermudagrass cultivars photograph taken on Mar. 1, 2018 before the first mowing. MACH-1 (also referred to as RL-1 herein) is in the background and Tifeagle is in the foreground. Tifeagle historically greened up first among the 3 major ultradwarf varieties. Here, RL-1 has beat Tifeagle on spring green up. (BOTTOM Photograph) RL-1 this spring in Tennessee. The picture with the Truck in the background has RL-1 in the foreground and Tifeagle in the background. The image was obtained on Mar. 16, 2018 after the first spring mowing.
Figure 6:
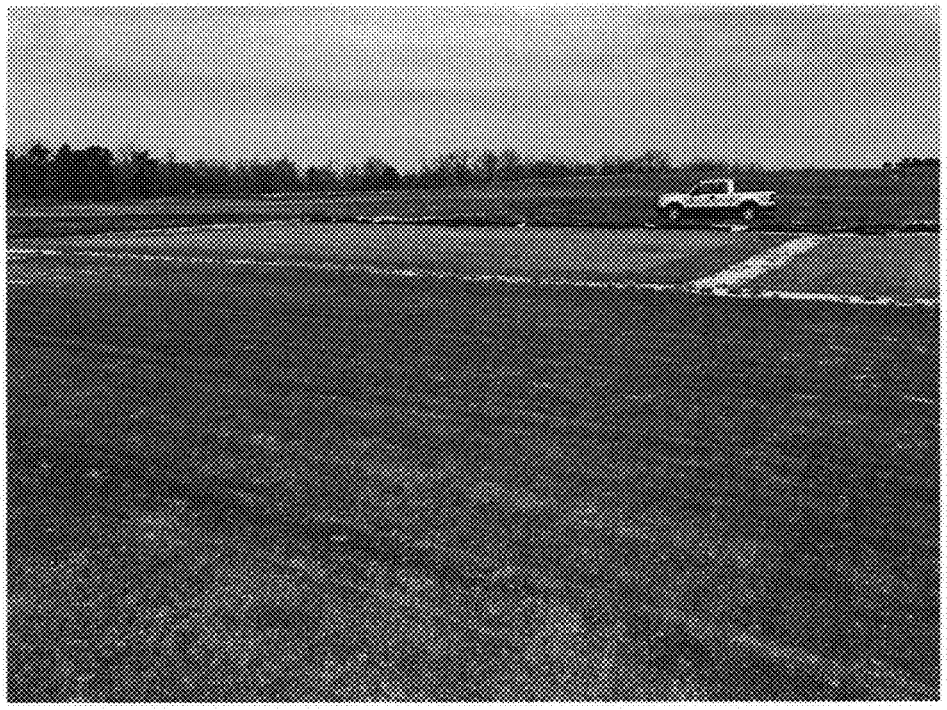
Figure 7:
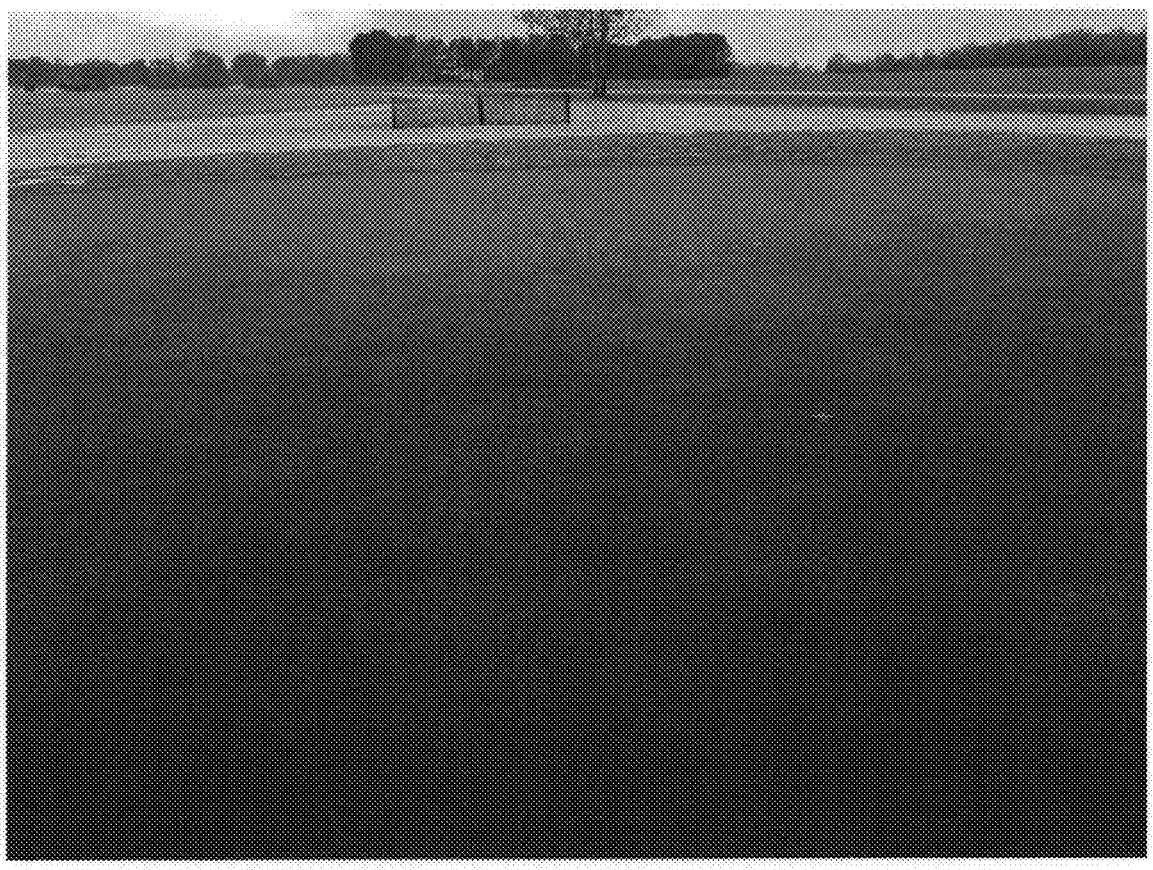
FIG. 7 is a photograph that shows a green planted with RL-1 in Camden, S.C.
Figure 8:
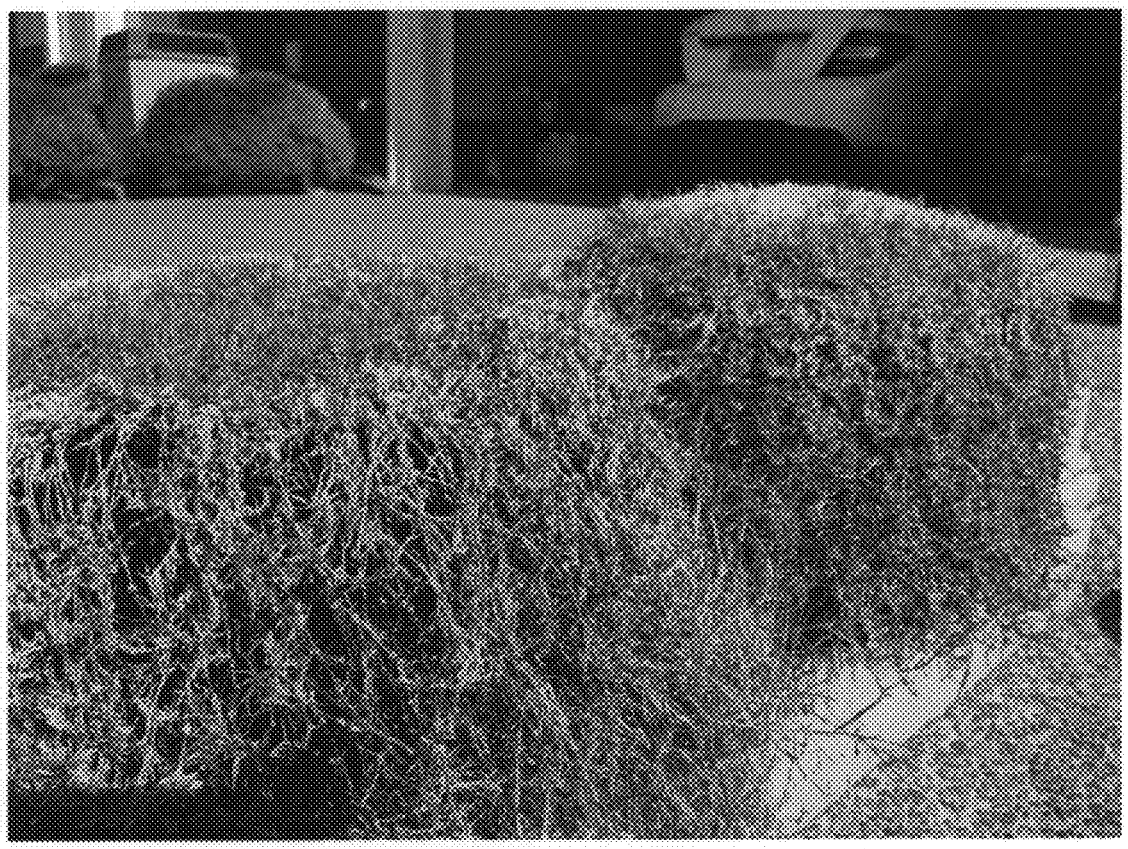
FIG. 8 attached picture shows a pot of Tifeagle with Bermudagrass scale, which are small white pearls on stolons (left side) and a pot of RL-1 without any scale (right side). The Tifeagle pot was intentionally placed close to the RL-1 pot to see if the scale would cross over. After one year, no scale formed on the RL-1. It is not common for Bermudagrass varieties to get scale, but it does happen especially when a Bermudagrass variety reaches terminal height. For example, cases of Bermudagrass scale have been reported on greens, for example greens planted with Tifeagle.
Figure 9:
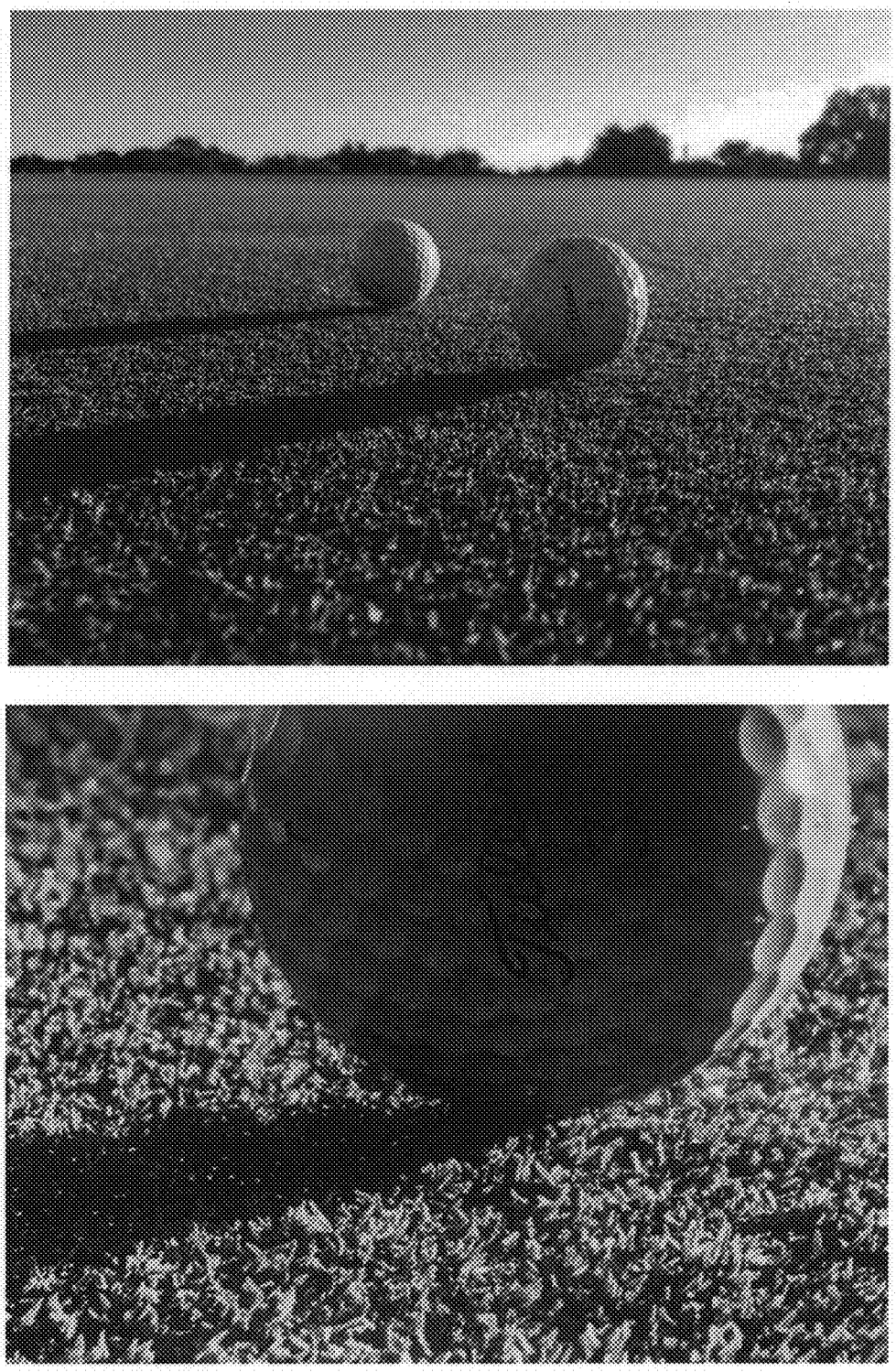
FIG. 9 is a photograph of a golf green planted with RL-1 on May 12, 2017. The golf ball sits on top of the grass and not down in the grass which allows for fast green speeds without mowing excessively low (TOP). RL-1 has a fine leaf blade texture and a dense surface. A very precisely applied growth regulator helps with these characteristics.
Figure 10:
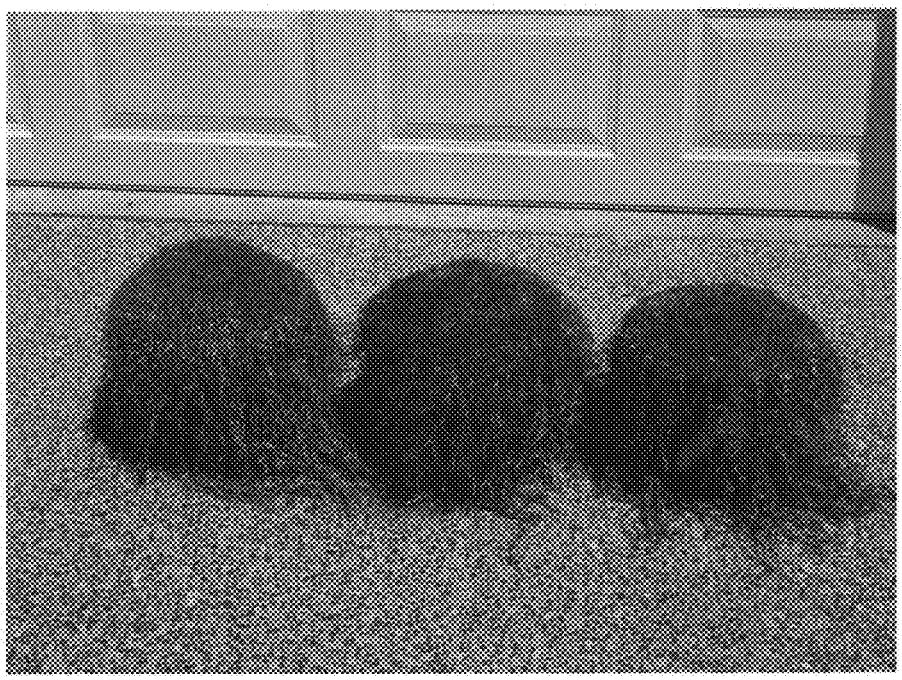
FIG. 10 are photographs showing bermudagrass varieties before being sprayed with 2% Roundup (TOP image) and 1 month after spraying with 2% Roundup (BOTTOM image; pots from left to right: RL-1, Tifeagle (middle), and MiniVerde). A pot with the RL-1 variety is on the left still displaying living green plant material; a pot with Tifeagle in the center shows nearly all browning; a pot with MiniVerde on the right also shows nearly all browning (Bottom photograph).
Figure 10:
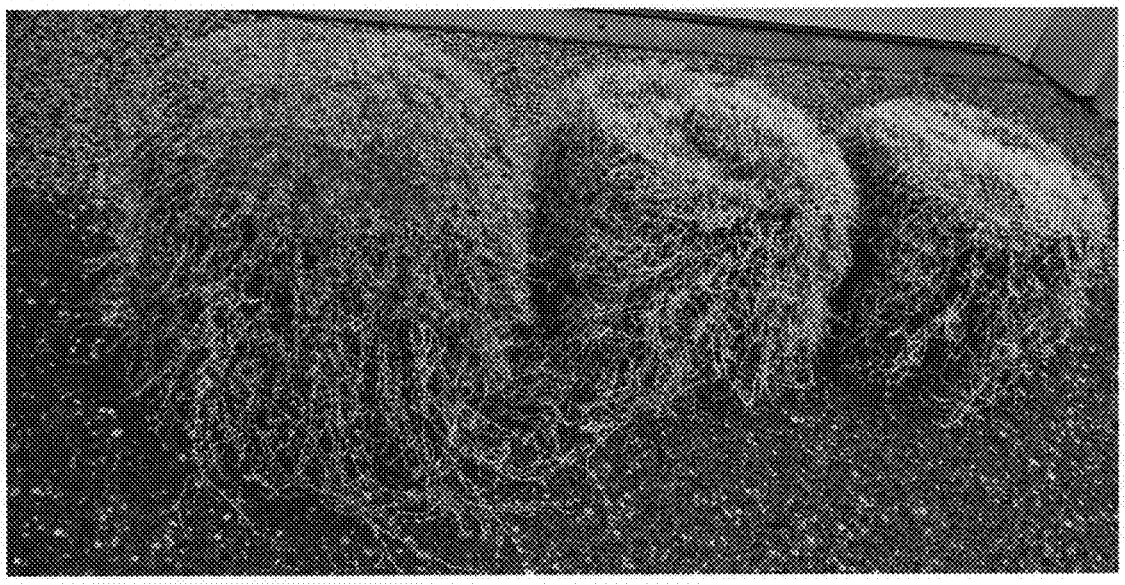
Figure 11:
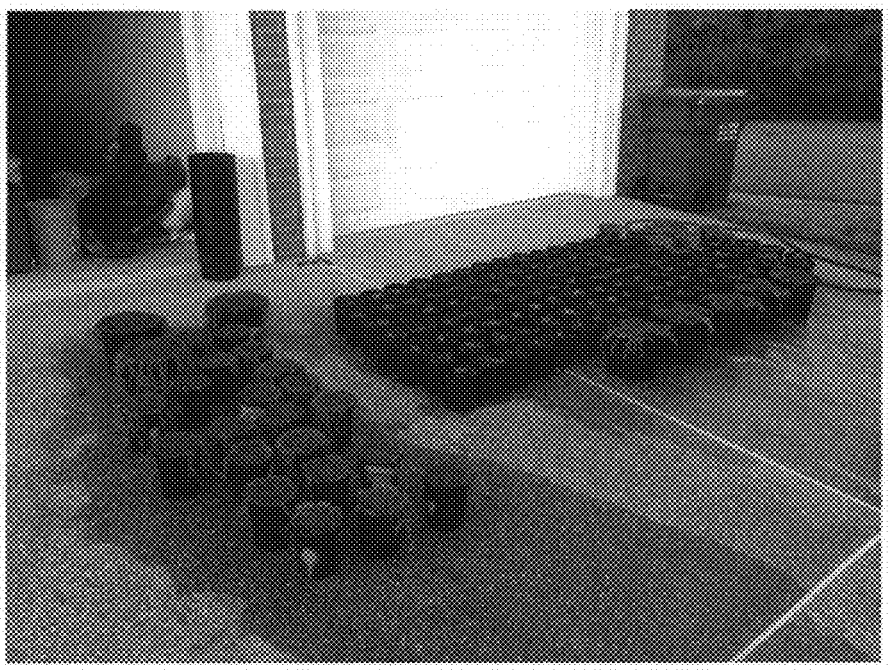
FIG. 11 are photographs showing RL -1 being propagated in pots on concrete.
Figure 11:
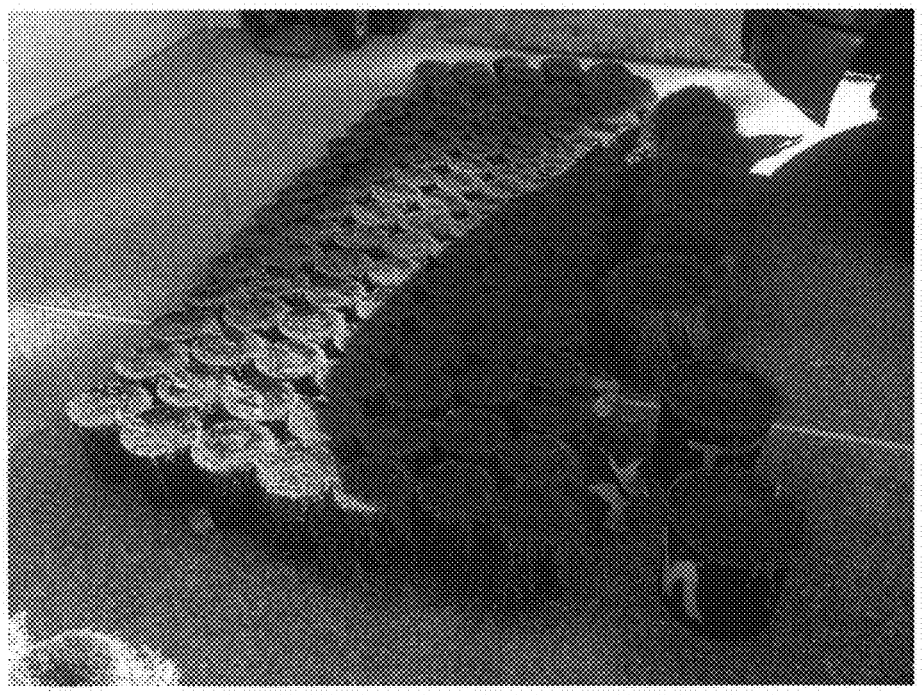
Figure 12:
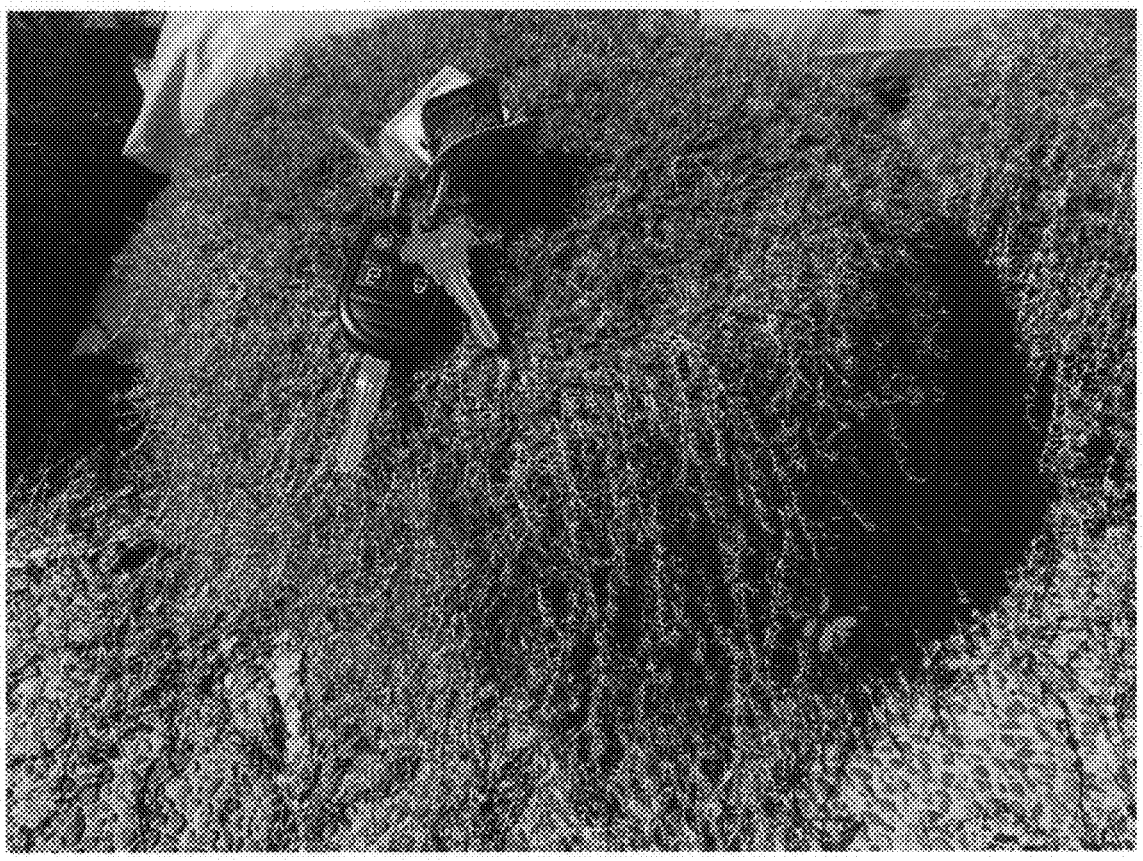
FIG. 12 is a photograph of RL-1 at terminal height, which also shows the short internode length.
Figure 13:
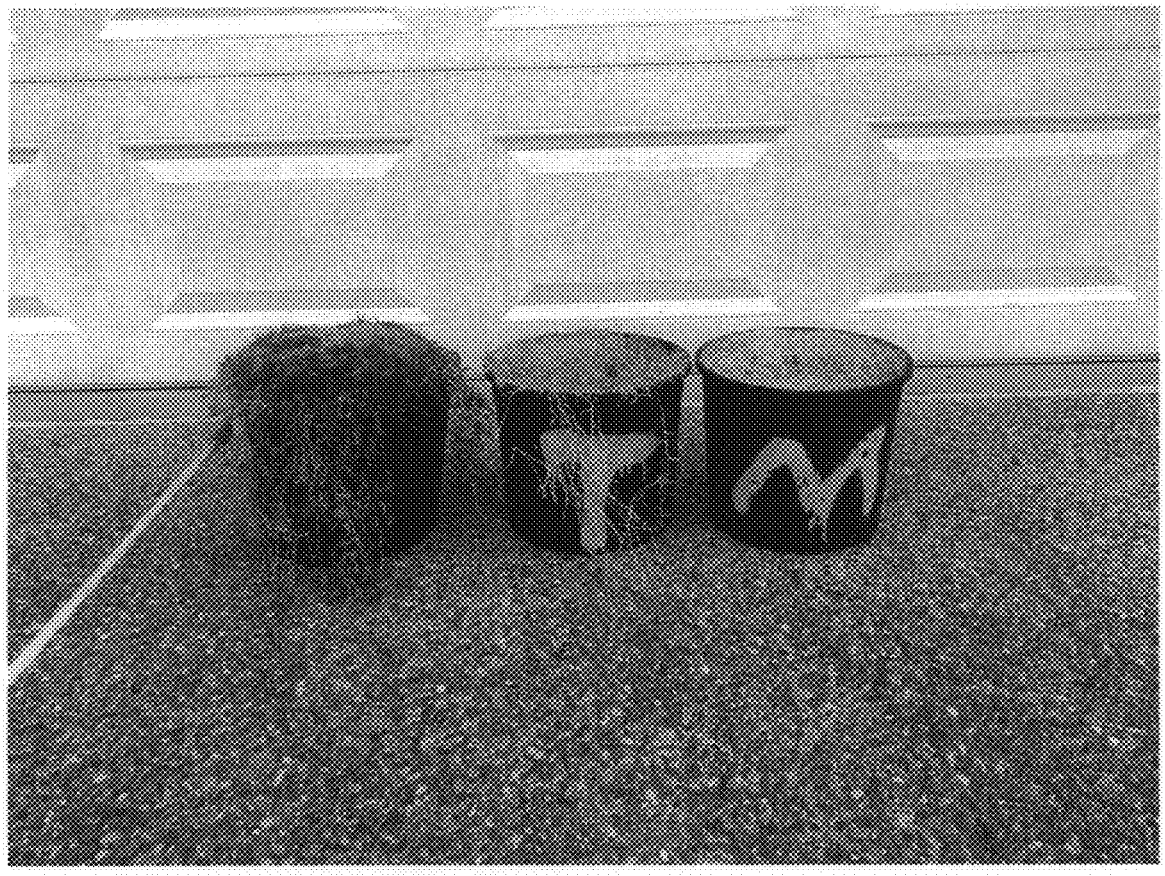
FIG. 13 is a photograph showing spring green up (2018) on Roundup trials. Left to right: RL-1 , Tifeagle, MiniVerde. Green blades are observed on the RL-1 variety.
Figure 14:
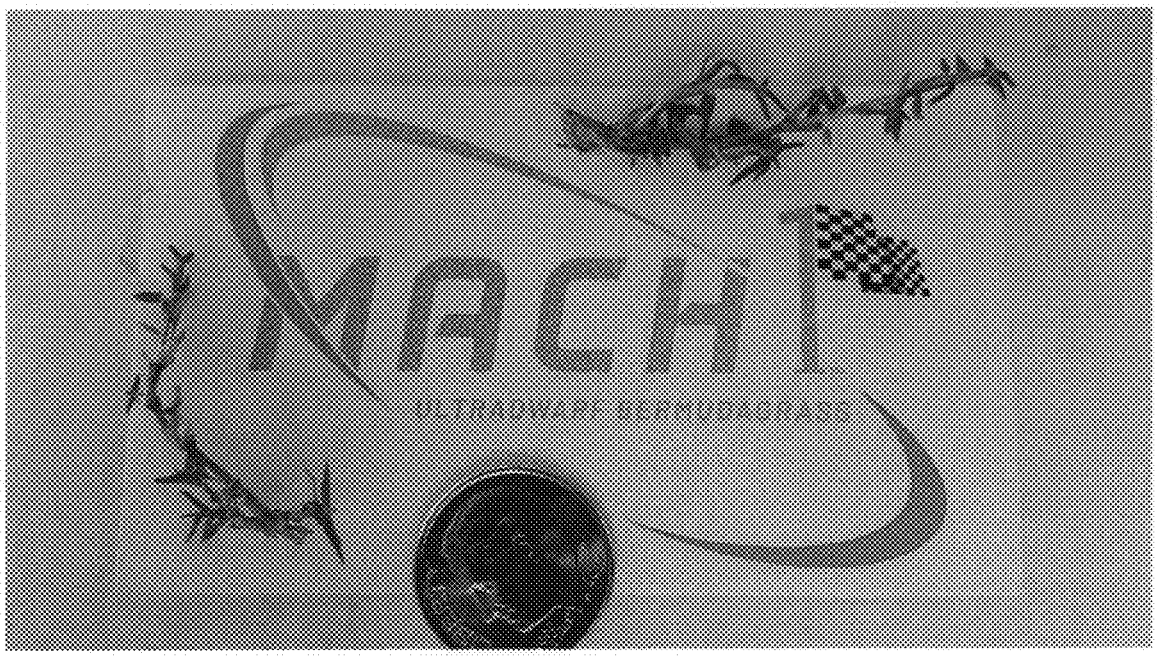
FIG. 14 is a photograph of sample RL-1 sprigs taken from a turf green in Camden, S.C. The image shows small leaves and internode length, when mowed at a height for turf greens (for example, 0.130 inches or 0.100 inches for tournament greens).

FIG. 3 is a picture of "purple spots" appearing on Bermudagrass cultivar Champion after 14 days of at/near freezing or below freezing temperatures (e.g., 32° F.). Unlike Champion, Tifdwarf and other Bermudagrass cultivars, 'ACE DWARF' (RL-1) did not turn purple in response to cold weather stress, indicating a tolerance for frigid temperatures.

Example 4—Frost tolerance of RL-1 ('ACE DWARF')

Fall color retention observations are typically used to assess the ability of a grass to hold color during the changing climatic conditions of fall, including chilling, frost, and shorter days and daylight hours. 'ACE DWARF' (RL-1) retained significantly more green color throughout fall than Champion or Tifdwarf.

Bermudagrasses are typically dormant in winter. However, 'ACE DWARF' (RL-1) held its color even in January when other cultivars such as Champion and Tifdwarf were significantly more dormant. This trait of 'ACE DWARF' (RL-1) would be very desirable in areas with mild winters and where temperatures often do not fall below freezing.

Example 5—Test Plots

A 5,400 $ft^2$ research green of MACH 1 (also referred to as 'ACE DWARF' (RL-1)) was established from sprigs during May 2017. Sprigs were provided and planted on May 22, 2017. A second research green of identical size was established using TifEagle sprigs from the University of Georgia on the same date. Since establishment, both areas have been maintained as golf course putting greens with respect to irrigation, fertilization, and mowing.

Mach 1 established rapidly during the summer of 2017 in Knoxville, Tenn. A direct comparison of establishment rates between Mach 1 and TifEagle could not be made at the site given that Mach 1 was planted at a sprigging rate 5× greater than TifEagle. All cultivars were mowed at a 0.125" height-of-cut within 11 weeks after sprigging. After both surfaces reached 100% cover during late summer, Mach 1 was found to have greater turfgrass quality than TifEagle, a result of leaf tissue being darker green in color. No plant growth regulators have been applied to either green since planting.

Air temperatures in Knoxville were quite severe during January 2018, with minimum temperatures falling below freezing for 21 days during the month. Moreover, the maximum air temperature did not exceed freezing for eight days during January 2018 as well. Using a typical golf course management protocol, both Mach 1 and TifEagle were covered with a winter protective cover (S&S Covers. Convington, Ga.) when air temperatures were forecasted to fall below 25° F. Both Mach 1 and TifEagle survived these hazardous winter conditions in Knoxville and emerged from dormancy during spring 2018. After emergence, the rate of spring green-up on Mach 1 exceeded that of TifEagle. Additional growth studies are ongoing on these plots.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A new and distinct Bermudagrass plant, substantially as herein shown, illustrated, and described.

* * * * *